United States Patent
Nakanishi et al.

(10) Patent No.: US 7,291,383 B2
(45) Date of Patent: Nov. 6, 2007

(54) SUPPORTS FOR SOLID PHASE EXTRACTION

(75) Inventors: Kazuki Nakanishi, Kyoto (JP); Shigeru Hanzawa, Kagamigahara (JP); Yousuke Sato, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 143 days.

(21) Appl. No.: 11/049,280

(22) Filed: Feb. 2, 2005

(65) Prior Publication Data

US 2005/0178709 A1 Aug. 18, 2005

Related U.S. Application Data

(63) Continuation-in-part of application No. 10/873,755, filed on Jun. 22, 2004, now abandoned.

(30) Foreign Application Priority Data

Jan. 23, 2004 (JP) ............................. 2004-015781
Jan. 19, 2005 (JP) ............................. 2005-011100

(51) Int. Cl.
*B32B 3/26* (2006.01)
*B01D 15/08* (2006.01)

(52) U.S. Cl. .................. 428/307.7; 428/304.4; 428/312.6; 210/198.2; 422/70

(58) Field of Classification Search ............ 428/304.4, 428/306.6, 307.7, 312.6; 422/69, 70; 210/198.2
See application file for complete search history.

(56) References Cited

U.S. PATENT DOCUMENTS

| 5,009,688 | A | 4/1991 | Nakanishi et al. |
| 5,624,875 | A | 4/1997 | Nakanishi et al. |
| 6,210,570 | B1 * | 4/2001 | Holloway ................ 210/198.2 |
| 6,531,060 | B1 * | 3/2003 | Nakanishi et al. ........ 210/198.2 |
| 6,770,584 | B2 * | 8/2004 | Barney et al. ............. 501/95.1 |
| 6,913,679 | B1 * | 7/2005 | Mathies et al. ............. 204/451 |
| 2002/0050470 | A1 * | 5/2002 | Jinno et al. .............. 210/198.2 |
| 2005/0023204 | A1 * | 2/2005 | Nakanishi et al. ........ 210/198.2 |
| 2005/0255989 | A1 * | 11/2005 | Soga et al. ................. 502/117 |

FOREIGN PATENT DOCUMENTS

| JP | 61-265567 A1 | 11/1986 |
| JP | 03-285833 A1 | 12/1991 |
| JP | 08-029952 B2 | 3/1996 |
| JP | 3317749 B2 | 6/2002 |
| JP | 2003-166983 A1 | 6/2003 |
| JP | 2004-115347 A1 | 4/2004 |
| WO | WO 9950654 A1 * | 10/1999 |

\* cited by examiner

*Primary Examiner*—John J. Zimmerman
*Assistant Examiner*—Aaron Austin
(74) *Attorney, Agent, or Firm*—Burr & Brown

(57) ABSTRACT

A support for solid phase extraction is provided for preventing the fracture of the porous body of the support and the space between the porous body and its container, and for processing various amounts of liquids to be processed while maintaining the ease of passage of liquid in use. The support for solid phase extraction comprises a ceramic substrate with one or more holes formed therein, and an inorganic porous material, filled in the hole or holes, which is produced by sol-gel transition accompanied by phase transition.

3 Claims, 5 Drawing Sheets

SUPPORTS FOR SOLID PHASE EXTRACTION

CROSS REFERENCE TO RELATED APPLICATION

This application is a continuation-in-part of U.S. application Ser. No. 10/873,755 filed Jun. 22, 2004 now abandoned and claims the benefit of Japanese Application 2004-015781, filed Jan. 23, 2004, and Japanese Application 2005-11100, filed Jan. 19, 2005, the entireties of which are incorporated herein by reference.

BACKGROUND OF THE INVENTION

1. Technical Field of the Invention

The present invention relates to a support for solid phase extraction.

2. Related Art Statement

Liquid-liquid phase extraction method has been used for the extraction of a sample from a liquid. The method, however, requires troublesome workings and a large amount of solvent. Additional problems may occur, for example, the solvent used may adversely affect environment and human bodies. Until now, a so called solid phase extraction method has been widely accepted. The method utilizes porous particles of silica or a synthetic polymer supplied by a modern advanced synthetic process. Such method requires easy working, a small amount of solvent, and can handle a large amount of samples by means of an automated system.

Fillers used for the solid phase extraction include inorganic materials such as silica gel whose surface is chemically modified with octadecyl group or the like to impart hydrophobic surface to the filler and chemically bonding type silica gel whose surface is chemically modified with an ion exchange group or the like to impart ion exchanging surface to the filler.

Further, according to Japanese Patent publication 2003-166,983A, a porous body is produced by phase transition in silica sol-gel system in a shrink tube to provide a support for solid phase extraction.

SUMMARY OF THE INVENTION

According to a support for solid phase extraction described in Japanese Patent publication 2003-166,983A, a silica porous body is produced by sol-gel transition accompanied by phase transition so that the body is filled in a thermal shrink plastic tube. The plastic tube is then shrunk with heat so that the tube is adhered onto the silica porous body therein to provide a support for solid phase extraction. The support for solid phase extraction is fitted to, for example, the tip of a syringe, which is driven to suck solution through the support. The syringe is driven again in the opposite direction to discharge the solution.

Such silica porous body produced by sol-gel transition accompanied by phase transition, however, has a considerably high porosity and a low mechanical strength. When the porous body is filled into the thermal shrink tube and the tube is shrunk by heat, it is difficult to handle and fix the silica porous body at a predetermined position in the tube. The silica porous body may be broken at a high incidence when the porous body is removed or fixed into the tube. Further, microcracks may be sometimes generated in the silica porous body due to a high pressure applied on the porous body from the tube. In particular, when the silica porous body has a diameter of, for example, 3 mm or smaller, the probability of the microcracks arises. When a pressure applied on the porous body by the tube is low, however, a space tends to be formed between the tube and the outer surface of the porous body.

The inventors further investigated a support for solid phase extraction having a cylinder and silica porous body produced in the hole of the cylinder by sol-gel transition accompanied by phase transition. In this case, however, as the inner diameter of the cylinder is larger, such as 1 mm or more, it has been proved that the following problems may occur due to the shrinkage of silica during the formation and drying of the silica porous body in the cylinder. That is, the porous body may be peeled off from the inner wall surface of the cylinder to leave a clearance between the porous body and the inner wall surface of the cylinder, so that the silica porous body may be easily removed from the cylindrical container when liquid is passed through the container. Further, when the inner diameter of the cylinder is made small enough for preventing the peeling of the silica porous body, a pressure loss of the support of the solid phase extraction is increased as the length of the cylinder is made larger. The ease of passage of liquid is deteriorated in use. There is a limit in obtaining a support for solid phase extraction having a large volume, to some degree, of the silica porous body and maintaining the ease of passage of liquid using the cylindrical container having one hole therein.

An object of the present invention is to provide a support for solid phase extraction for preventing the fracture of the porous body of the support and the space between the porous body and its container, and for processing various amounts of liquids to be processed while maintaining the ease of passage of liquid in use.

The present invention provides a support for solid phase extraction comprising a ceramic substrate with a hole formed therein and an inorganic porous material filled in the hole produced by sol-gel transition accompanied by phase transition.

According to the support for solid phase extraction of the present invention, an inorganic porous material produced by sol-gel transition accompanied by phase transition is provided as an extracting phase in holes of a ceramic substrate.

According to the present invention, it is unnecessary to directly handle a porous body produced by sol-gel transition having a low strength, so that the fracture of the silica porous body can be avoided. It is further possible to avoid the compression of the porous body with a thermal shrink tube, so that microcracks in the porous body and the formation of the clearance due to the compression can be avoided.

Further, when a porous body is produced in the inner space of a ceramic cylindrical body by sol-gel transition accompanied by phase transition and when the inner space has a diameter of, for example, greater than 1 mm, a space may easily occur between the porous body and the inner wall surface of the cylindrical body. Further, when a ceramic substrate is made longer and the silica porous body is produced therein for improving the volume of the porous body, the pressure loss in the support for solid phase extraction is increased so the ease of passage of liquid is deteriorated. According to the present invention, however, it is possible to change the volume of the extraction phase by changing the diameter and number of the holes of the ceramic substrate, while the ease of passage of liquid in use is maintained. For example, a plurality of holes enough small for avoiding the formation of the clearance may be formed for generating the porous body in each of the holes. It is thus possible to provide a support for solid phase extraction, so that the formation of the space can be pre-

DETAILED DESCRIPTION OF THE INVENTION

Figure 1:
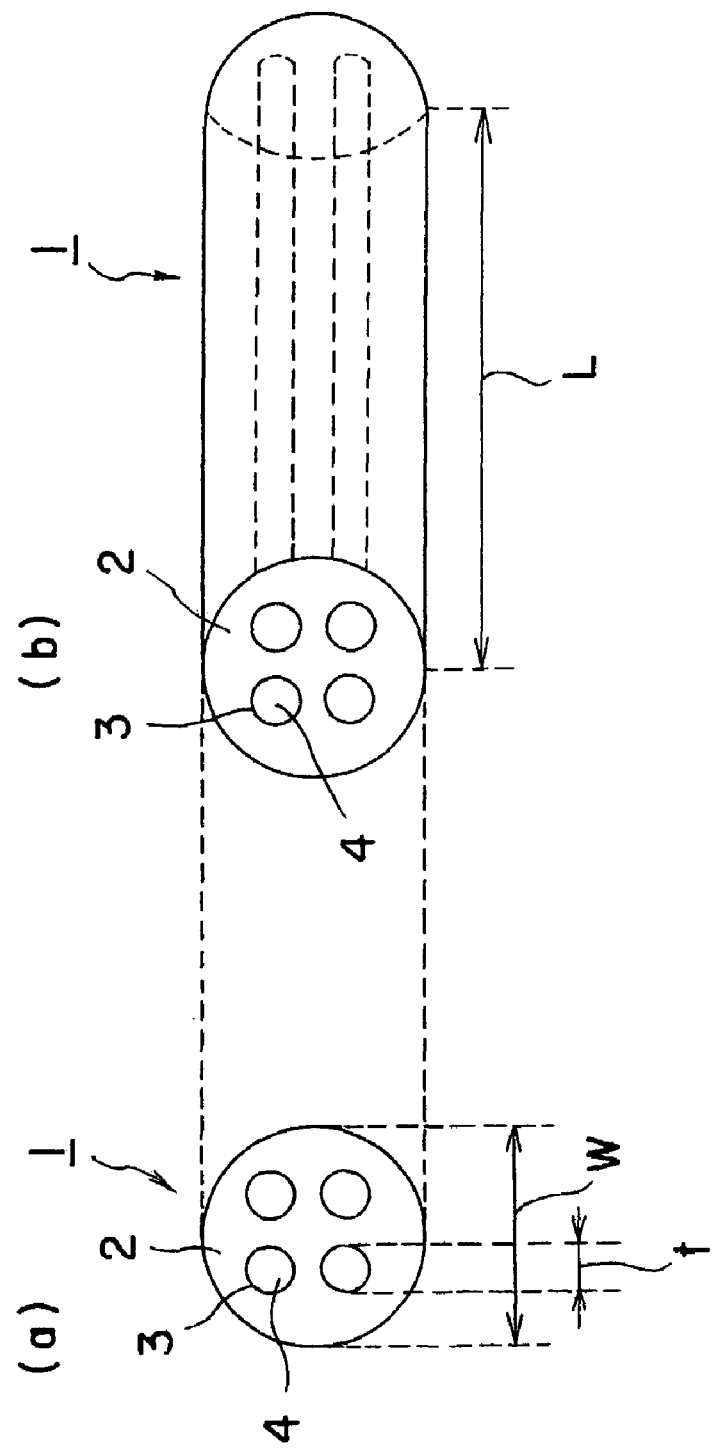
FIG. 1(a) is a front view showing a support 1 for solid phase extraction according to the present invention.
FIG. 1(b) is a perspective view showing the support 1 for solid phase extraction.

FIG. 1(a) is a front view showing a support 1 for solid phase extraction according to the present invention, and FIG. 1(b) is a perspective view of the support 1 for solid phase extraction. The support 1 for solid phase extraction has a ceramic substrate 2. According to the present invention, the ceramic substrate 2 may be, and not limited to, a ceramic honeycomb substrate, The ceramic substrate 2 has a predetermined number of holes 3 formed therein at predetermined positions. An extraction phase 4 of an inorganic material produced by sol-gel transition is filled in each of the holes 3.

One or a plurality of the holes 3 may be provided. The dimension of each hole 3 may be variously changed. Further, the width "W" of the substrate 1 is not particularly limited. The diameter "t" of each hole 3 may preferably be 1 mm or smaller, more preferably be 0.2 mm or smaller and most preferably be 0.1 mm or smaller, on the viewpoint of preventing the peeling off of the extraction phase 4 from the hole 3. Although the lower limit of the diameter "t" of the hole 3 is not particularly limited, it may preferably be 5 micrometer or larger, on the viewpoint of forming the inorganic porous material produced by sol-gel transition accompanied with phase transition in the hole while preserving the characteristic pore structure. Further, although the length "L" of the support for solid phase extraction is not particularly limited, the ease of passage of liquid is deteriorated as the length is made larger. It is thus needed to design the length considering the convenience of handling.

The material of the ceramic substrate is not particularly limited, and may be inorganic oxides such as silicon oxide, aluminum oxide, titanium oxide, zirconium oxide and cordierite, or ceramics such as silicon carbide, silicon nitride and so on.

Further, in the ceramic substrate, the inner wall surface facing the hole may be subjected to a surface treatment for adjusting the adhesion of the ceramics and the porous body formed in the hole. Such surface treatments include sol-gel process, chemical vapor deposition, physical vapor deposition, sputtering, plating or the other various methods.

According to the present invention, the porous body 4 is generated by sol-gel transition accompanied with phase transition in the hole 3 of the ceramic substrate 1. For performing the reaction, a solution containing a precursor of a network-forming component is produced, the precursor in the solution is then reacted, for example hydrolyzed, to generate sol, and the sol is gelled (solidified). The whole process is called "sol-gel transition". Phase transition of a phase rich in the network-forming component for causing gellation (gel phase) and a phase rich in a solvent component irrelevant of gellation (solvent phase) are induced parallel to sol-gel transition. As a result, the gel forms a network like structure, so that the solvent phase is dried to remove the solvent to obtain the porous body having the open pores.

In the sol-gel reaction system, phase separation occurs as time passes by. That is, the system is separated to a phase rich in a network-forming component causing gel formation (gel phase) and a phase rich in a solvent component irrelevant of the gel formation (solvent phase). In the formation of the phases, each component is diffused inversely with respect to the gradient of concentration based on a difference of chemical potential as the driving force. The movement of substances is continued until each phase reaches an equilibrium composition specified at a given temperature and pressure.

After the sol-gel transition reaction is terminated in the solvent, the resulting wet gel is washed or the solvent is exchanged with another solvent. The solvent is then removed to obtain an inorganic porous material. If required, the inorganic porous material may be heat treated at an appropriate temperature.

The pore size (diameter) of the open pores of the porous body may preferably be 100 nm or more. Such macropores are formed in regions occupied by the solvent phase generated in the phase separation process. When a so-called co-continuous structure, in which the solvent and gel phases are both interconnected, respectively, a considerably sharp size distribution can be obtained.

The porous material may be made of an inorganic material not particularly limited. A metal oxide is particularly preferred. Such metal oxide includes silicon oxide, titanium oxide, zirconium oxide, and alumina. Two or more kinds of metal oxides may be used at the same time. When silica is used as the metal oxide, the adhesion of the metal oxide and the inner wall surface of the ceramic substrate can be further improved by chemical bonding.

The precursor for the network-forming component for causing gellation in the sol-gel reaction includes the following:

(1) A metal alkoxide, a metal complex, a metal salt, a metal alkoxide modified with an organic substance, a metal alkoxide with cross linked organic substance, or an organic metal alkoxide organic replaced with an alkyl group;

(2) A partially hydrolyzed product of a metal alkoxide, a metal complex, a metal salt, a metal alkoxide modified with an organic substance, a metal alkoxide with cross linked organic substance, or an organic metal alkoxide replaced with an alkyl group;

(3) A polymer product of partial polymerization of a metal alkoxide, a metal complex, a metal salt, a metal alkoxide modified with an organic substance, a metal alkoxide with cross-linking organic substance, or an organic metal alkoxide partly substituted with an alkyl group; and (4) Sol-gel transition by means of changing the pH of water glass or aqueous solution of the other silicates.

Further in a more specific manufacturing process, a water soluble polymer is dissolved in an acidic aqueous solution. The precursor, more preferably a metal compound having a hydrolyzable functional group, is then added to the solution to perform hydrolysis. The degree of polymerization of the precursor of the network-forming component is gradually increased so that the miscibility between the gel phase containing the network-forming component and solvent phase containing water as the main component, or solvent phase containing a water soluble polymer as the main component is reduced. During the process, spinodal decomposition is induced parallel to gellation which is proceeded by the hydrolysis and polymerization of the network-forming component in the solvent. The product is then dried and heated.

Any water soluble polymer may be used, as far as it may be used for producing an aqueous solution having an appropriate concentration and may be uniformly dissolved into a reaction system containing an alcohol generated from a metal compound having a hydrolyzable functional group. Specifically, it is preferred the sodium salt or potassium salt of polystyrene sulfonate as the metal salt of a polymer; polyacrylic acid as an acid of a polymer dissociated to generate a polyanion; polyallyl amine and polyethylene imine as the base of a polymer dissociated to generate a polycation in aqueous solution; polyethylene oxide as a neutral polymer having an ether bond in the main chain; or polyvinyl pyrrolidone or the like. Further, instead of the organic polymer, formamide, a polyalcohol, and a surfactant may be used. In this case, glycerin as the polyalcohol and polyoxyethylene alkyl ether as the surfactant are most preferred.

The metal compound having a hydrolyzable functional group may be a metal alkoxide or the oligomer. The alkoxide or oligomer may preferably have an alkyl group having a small number of carbon atoms such as methoxy, ethoxy, propoxy group or the like. The metal therefor is that constituting the metal oxide to be finally produced, such as Si, Ti, Zr or Al. One or more metals may be used. On the other hand, the oligomer may be uniformly dissolved or dispersed in an alcohol and specifically the number of repetition may be up to about 10. Further, an alkyl alkoxy silane in which some of the alkoxy groups in a silicon alkoxide are replaced with an alkyl group, and the oligomer having a repetition number up to about 10 may be preferably used. Further, a metal alkoxide replaced with alkyl group containing titanium, zirconium, aluminum or the like as the main metal element instead of silicon may be used.

Further, the acidic aqueous solution may preferably be 0.001 N or more of a mineral acid, normally hydrochloric acid, nitric acid or the like, or 0.01 N or more of an organic acid such as formic acid, acetic acid or the like.

The hydrolysis and polymerization reactions can be performed by holding the solution at a temperature of room temperature to 40 or 80° C. at 0.5 to 5 hours. The gellation and phase separation may be caused during the process.

The inorganic porous body constituting the extraction phase according to the present invention may be chemically modified with a functional group. Although such functional group may be non-polar groups such as octadecyl and phenyl groups or polar groups such as amine and nitrile, it may be any functional groups commonly used for chemical bonding type silica gel for solid phase extraction.

Although applications of the support for solid phase extraction according to the present invention are not particularly limited, it may be used for analysis of environment-related samples, medical samples or the like due to the characteristics as a filler for solid phase extraction. That is, the support may be used for concentrating dilute object substance contained in a trace amount in the sample, and/or, for efficiently removing contaminants coexisting in the sample.

For example, the following applications may be listed.
(1) A trace amount of an object substance contained in a sample is concentrated.
(2) A contaminant coexisting with an object substance in a sample is removed.
(3) The inventive support is utilized in a treatment before and/or after various kinds of analysis.
(4) The inventive support is utilized for measurement of identification or quantification of a drug sample in serum.
(5) The inventive support is utilized for measuring toxic substances such as agricultural chemicals in water samples taken from rivers.
(6) The inventive support is utilized for measuring agricultural chemicals residue in agricultural products.
(7) The inventive support is utilized for measuring drugs in serum.

EXAMPLES

Example 1

(Production of a Ceramic Substrate)

5 weight parts of polyvinyl alcohol was added as a binder to 100 weight parts of alumina powder having a mean particle diameter of 0.5 micrometer, and then blended with a blender to obtain clay (slurry). The clay was supplied into an extruder and extruded in a rate of 10 mm/s and then cut to obtain an elongate body having a length of about 100 mm, which was then dried at 40° C. in a drier for 1 day to obtain a shaped body (dried body). The temperature of the thus obtained shaped body (dried body) was elevated to 200° C. for 1 hour, maintained at 200° C. over 1 hour, elevated to 300° C. over 1 hour and to 1600° C. over 6 hours, and kept at 1600° C. for 2 hours. The thus obtained sintered body was naturally cooled to room temperature and removed. The thus obtained sintered body was cut out to obtain a ceramic substrate having a length of 20 mm, an outer diameter "W" of about 0.8 mm φ and four holes each having an diameter "t" of about 0.1 mm φ.

(Formation of Adsorption Phase in the Inside of the Ceramic Substrate)

0.8 g of polyethylene oxide (supplied by Aldrich Co.) as the water soluble polymer and 1.0 g of urea were uniformly dissolved in 10 ml of 0.01 mol/L acetic acid solution to obtain a solution. After that, the solution was stirred for 30 minutes under cooling with ice, and 4.0 ml of tetramethoxysilane (a precursor for a network-forming component: supplied by Shin-Etsu Chemical Co., Ltd.) was added under stirring to perform hydrolysis. The thus obtained transparent solution was filled into the holes of the ceramic substrate. The substrate was then held in a constant temperature bath at 40° C. until the solution was solidified. The thus obtained gel was aged for about 24 hours at 40° C. The substrate was then held at 120° C. for 3 hours and then dried at 40° C. to evaporate and remove the solvent. The ceramic substrate was heat treated at 330° C. to decompose organic substances to obtain an extraction phase composed of porous silica. After that, the ceramic substrate having the extraction phase was immersed in toluene solution for 12 hours, and then immersed in toluene solution with octadecyl trichlorosilane added so that the surface of silica was chemically modified with octadecyl group for 24 hours to obtain a support for solid phase extraction.

(Observation of Microstructure of a Support 1 for Solid Phase Extraction)

Figure 2:
FIG. 2 is a photograph, taken by an electron microscope, of the support 1 for solid phase extraction.
Figure 3:
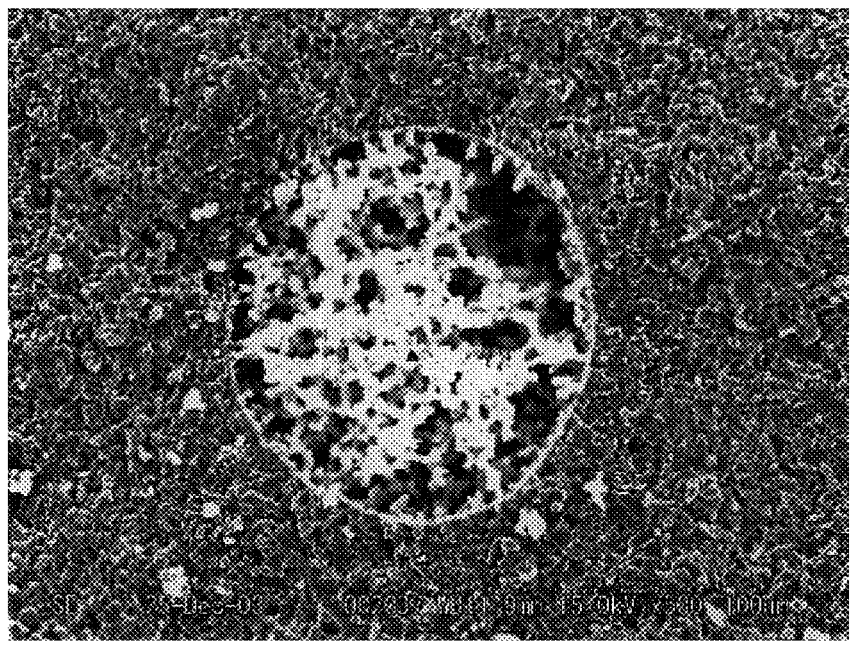
FIG. 3 is a photograph, taken by an electron microscope, of the support 1 for solid phase extraction whose hole is enlarged.

FIG. 2 is a photograph taken by an electron microscope of the thus obtained support for solid phase extraction according to the present invention. Four holes are provided in the support according to the present example. Silica is generated in each of the holes. FIG. 3 is a photograph showing an enlarged view of the inside of the hole in the support for solid phase extraction of FIG. 2. It is observed a microstructure in which silica is continuously formed to dendritic form. It was further proved that considerably large pores are continuously and uniformly formed.

(Experiment of Solid Phase Extraction)

The support for solid phase extraction was connected with a syringe to perform an experiment of solid phase extraction. Sodium chloride and tris(hydroxymethyl)amino methane were added to obtain aqueous solution, whose pH was adjusted at 7 with hydrochloric acid to obtain an equilibrating solution. Cytochrom c was added to the equilibrating solution to obtain a sample solution. After the support for solid phase extraction was pre-wet with acetonitrile solution, the equilibrating solution was sucked and discharged five times to equilibrating the support. After 5 μl of the sample solution was sucked, the solution was then discharged so that Cytochrom c was adsorbed onto the support. The equilibrating solution was then sucked and discharged five times to sufficiently wash the support. 5 μl of 0.1% trifluoro acetic acid and 60% acetonitrile aqueous solution were sucked and discharged to obtain extract.

(Analysis of Extract)

Figure 4:
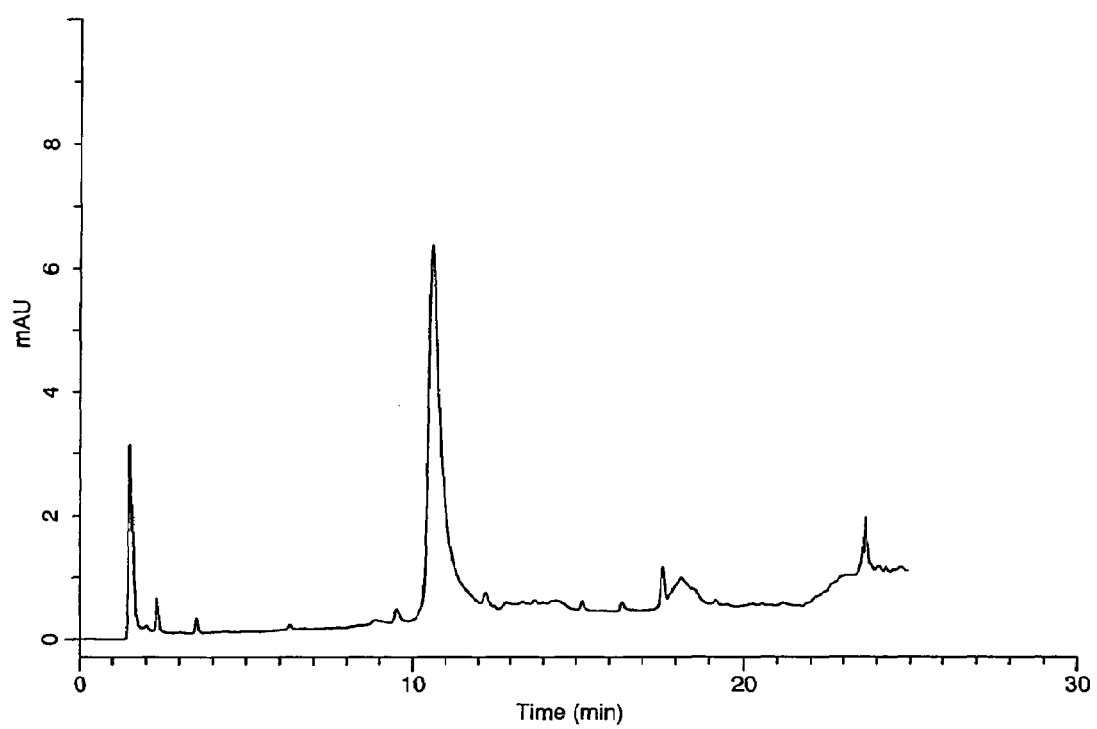
FIG. 4 is a chart showing the results of analysis of extract.

The extract was analyzed with a high performance liquid chromatography in the gradient analysis, using a column (Chromolith performance RP-18 (100 mm×4.6 mm I. D.), a detector (UV 280 nm), and a mobile phase (aqueous solution containing 0.1% trifluoro acetic acid, and aqueous solution containing 0.1% trifluoro acetic acid and 90% acetonitrile. The results of the analysis of the extract were shown in FIG. 4. A peak corresponding to Chytochrom c was detected in a range of 10 min. to 11 min. It was thus proved that the extraction was carried out using the support for solid phase extraction of the present invention. The yield was calculated and proved to be about 100 percent.

Comparative Example 1

A porous body of silica having a diameter φ of about 200 μm and a length of 20 mm was produced, for providing a support for solid phase extraction having the same volume of silica porous body and the same level of ease of passage of liquid as the example 1. Solution having the same composition as that in the example was flown into a cylindrical mold made of polypropylene having an inner diameter of 250 μm and a length of 25 mm. The mold was sealed at both ends and held in a constant bath maintained at 40° C., so that the transparent solution was solidified. The solid was aged at 40° C. for about 24 hours. After the aging, the ceramic substrate was held at 80° C. for 24 hours. The sealing of the cylindrical mold of polypropylene was opened and dried at 40° C. to remove the solvent. The thus produced silica porous body was removed from the cylindrical mold of polypropylene for a subsequent thermal treatment at 400° C. However, the silica porous body was broken when the body was removed from the container. It was thus impossible to insert the silica porous body into a thermal shrink tube to produce a support for solid phase extraction.

Comparative Example 2

A porous body of silica having a diameter φ of about 500 μm and a length of 20 mm was produced, for providing a support for solid phase extraction having the larger volume of silica porous body and the same level of ease of passage of liquid as the comparative example 1. Solution having the same composition as that in the example was flown into a cylindrical mold made of polypropylene having an inner diameter of 650 μm and a length of 25 mm. The mold was sealed at both ends and held in a constant bath maintained at 40° C., so that the transparent solution was solidified. The solid was aged at 40° C. for about 24 hours. After the aging, the ceramic substrate was held at 80° C. for 24 hours. The sealing of the cylindrical mold of polypropylene was opened and dried at 40° C. to remove the solvent. The thus produced silica porous body was removed from the cylindrical mold of polypropylene for a subsequent thermal treatment at 400° C. The porous body was then contained in a thermal shrink polyethylene tube, and heat treated at 100° C. for 10 minutes to produce a support for solid phase extraction.

The thus obtained support for solid phase extraction was connected to a syringe and subjected to an experiment for solid phase extraction according to the same procedure as the example 1. It was, however, proved that the silica porous body was broken during the handling and fixing in the thermal shrink tube so that problems occur. For example, a part of the silica porous body inside was peeled off when the solution was passed through in the pre-wetting and equilibrating steps. Further, according to the present experiment for solid phase extraction, a time period for the heat treatment of the tube was reduced for lowering the pressure in the thermal shrinkage of the tube. It was proved, however, that the adherence of the tube and silica porous body was insufficient so that the silica porous body inside of the tube was peeled off when the solution was passed through the porous body.

Further, a porous body of silica having a diameter φ of about 1.5 mm and a length of 20 mm was produced, for providing a support for solid phase extraction having a still larger volume of silica porous body and the same level of ease of passage of liquid as the examples, according to the same procedure as described above. It was proved that the silica porous body was broken during the handling and thermal shrinkage in the thermal shrink tube, so that a part of the silica porous body was peeled off when the solution was passed through the porous body.

Example 2

The clay (slurry) produced in the Example 1 was supplied into an extruder and extruded in a rate of 10 mm/s and then cut to obtain an elongate body having a length of about 100 mm, which was then dried at 40° C. in a drier for 1 day to obtain a shaped body (dried body). The temperature of the thus obtained shaped body (dried body) was elevated to 200° C. for 1 hour, elevated to 1600° C. over 6 hours, and held at 1600° C. for 2 hours. The thus obtained sintered body was naturally cooled to room temperature and taken. The thus obtained sintered body was cut out to obtain a ceramic substrate having a length of 20 mm, an outer diameter "W" of about 1.0 mm φ and four holes each having a diameter "t" of about 0.2 mm φ.

The solution having the same composition as that in the Example 1 was blended and prepared. The thus obtained transparent solution was supplied into the holes of the ceramic substrate. A support for solid phase extraction was obtained according to the same conditions as the Example 1.

Figure 5:
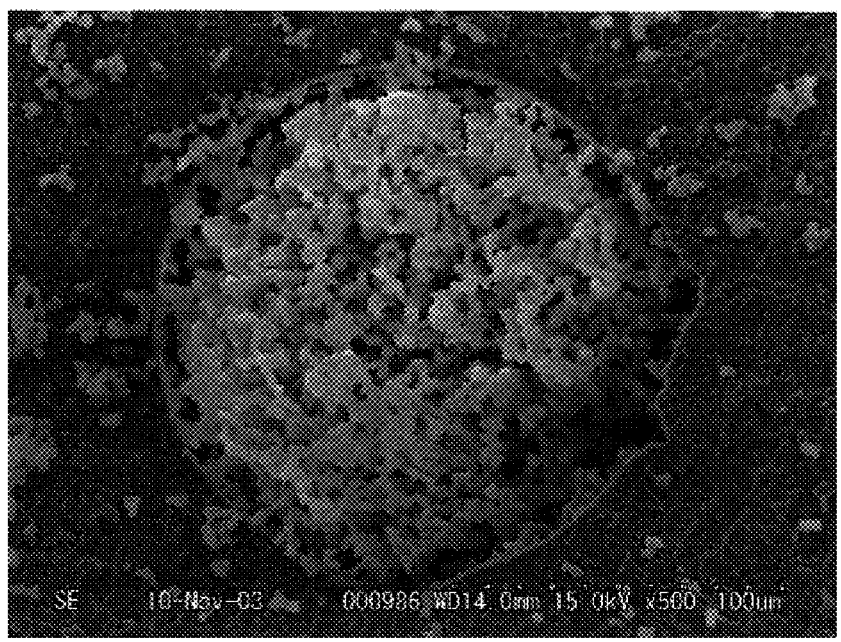
FIG. 5 is a photograph taken by an electron microscope of the inside of the hole (enlarged view) of a support for solid phase extraction, according to example 2.

FIG. 5 is a photograph taken by an electron microscope of the inside of the hole (enlarged view) of the thus obtained support for solid phase extraction according to the present invention. It is observed a microstructure in which silica is continuously formed to dendritic form. It was further proved that considerably large pores are continuously and uniformly formed.

The support for solid phase extraction was connected with a syringe to perform an experiment of solid phase extraction. The experimental procedure was the same as that in the Example 1. 20 μl of the sample solution was sucked so that the solution was adsorbed onto the support. The equilibrating solution was then sucked and discharged five times to sufficiently wash the support. 20 μl of 0.1% trifluoro acetic acid and 60% acetonitrile aqueous solution were sucked and discharged to obtain extract.

The extract was analyzed according to the same procedure as the Example 1. A peak corresponding to Chytochrom c was detected in a range of 10 min. to 11 min, as the Example 1. It was thus proved that the extraction was carried out using the support for solid phase extraction of the present invention. The yield was calculated and proved to be about 100 percent.

Example 3

It was obtained a ceramic substrate having an outer diameter "W" of about 6.0 mm φ and four holes each having a diameter "t" of about 1.0 mm φ, according to the same procedure as the Example 1. The solution same as the Example 1 was supplied into the holes to obtain a support for solid phase extraction according to the same procedure as the Example 1. The support for solid phase extraction was connected with a syringe to perform an experiment of solid phase extraction. The experimental procedure was the same as that in the Example 1. 400 μl of the sample solution was sucked and adsorbed onto the support. The equilibrating solution was then sucked and discharged five times to sufficiently wash the support. 400 μl of 0.1% trifluoro acetic acid and 60% acetonitrile aqueous solution were sucked and discharged to obtain extract.

The extract was analyzed according to the same procedure as the Example 1. A peak corresponding to Chytochrom c was detected in a range of 10 min. to 11 min, as the Example 1. It was thus proved that the extraction was carried out using the support for solid phase extraction of the present invention. The yield was calculated and proved to be about 100 percent.

Example 4

It was obtained a ceramic substrate having an outer diameter "W" of about 2.0 mm φ and one hole having an diameter "t" of about 1.5 mm φ, according to the same procedure as the Example 1. The solution same as the Example 1 was supplied into the holes to obtain a support for solid phase extraction according to the same procedure as the Example 1. Five samples were obtained according to the above process. The inside of each hole of the thus obtained samples was observed. As a result, it was proved that silica was peeled from the ceramic substrate in a part of the inner wall surface facing the hole, in the three of the five samples.

The support for solid phase extraction was connected with a syringe to perform an experiment of solid phase extraction. The experimental procedure was the same as that in the Example 1. 100 μl of the sample solution was sucked and adsorbed onto the support. The equilibrating solution was then sucked and discharged five times to sufficiently wash the support. 100 μl of 0.1% trifluoro acetic acid and 60% acetonitrile aqueous solution were sucked and discharged to obtain extract.

The extract was analyzed according to the same procedure as the Example 1. A peak corresponding to Chytochrom c was detected in a range of 10 min. to 11 min, as the Example 1. The yield was calculated and proved to be about 10 percent.

As described above, when the diameter of the hole exceeds 1.0 mm, there is a case that silica may be peeled from the inner wall surface facing the hole so that may become difficult to recover a target substance at a yield of 100 percent in such support.

The invention claimed is:

1. A support for solid phase extraction, comprising:
   a ceramic elongate honeycomb substrate having a plurality of holes formed therein, each said hole having a diameter defined by a distance between diametrically opposed points on an inner wall surface facing said at least one hole, said diameter of each said hole being less than or equal to 1 mm; and
   an inorganic porous material filling said at least one hole, said inorganic porous material being produced by sol-gel transition accompanied by phase transition;
   wherein said elongate honeycomb substrate comprises one of silicon oxide, aluminum oxide, titanium oxide, zirconium oxide, cordierite, silicon carbide and silicon nitride;
   wherein said porous material comprises one of silicon oxide, titanium oxide, zirconium oxide and alumina; and
   wherein each said hole has a longitudinal extension axis that is parallel to a longitudinal extension axis of said elongate honeycomb substrate, said longitudinal extension axis of each said hole being substantially continuous along said longitudinal extension axis of said elongate honeycomb substrate between first ends of said holes and opposed second ends of said holes.

2. The support for solid phase extraction of claim 1, wherein said inorganic porous material comprises silica.

3. The support for solid phase extraction of claim 1, wherein said ceramic elongate honeycomb substrate comprises alumina.

* * * * *